(12) United States Patent
Garraffa et al.

(10) Patent No.: US 7,181,778 B1
(45) Date of Patent: Feb. 27, 2007

(54) DIVE MASK HAVING REPLACEABLE LENSES AND FRAME BONDED INTO A RUBBER SKIRT

(76) Inventors: Dean R. Garraffa, 15 Nerval, Newport Coast, CA (US) 92657; Douglas J. Toth, 503 Via Florida, San Clemente, CA (US) 92672

( * ) Notice: Subject to any disclaimer, the term of this patent is extended or adjusted under 35 U.S.C. 154(b) by 0 days.

(21) Appl. No.: 11/228,667

(22) Filed: Sep. 16, 2005

(51) Int. Cl.
*A61F 9/02* (2006.01)
(52) U.S. Cl. ............ 2/428; 2/426; 2/427; 2/431; 2/446
(58) Field of Classification Search ........... 2/428, 2/427, 426, 431, 446
See application file for complete search history.

(56) References Cited

U.S. PATENT DOCUMENTS

| | | | |
|---|---|---|---|
| 2,368,303 A * | 1/1945 | Johnston ............ 2/426 |
| 3,415,596 A * | 12/1968 | Carmichael ............ 351/131 |
| 5,682,621 A * | 11/1997 | Park ............ 2/441 |
| 6,192,523 B1 * | 2/2001 | Pan ............ 2/428 |
| 6,349,419 B1 * | 2/2002 | Chiang ............ 2/428 |
| 6,484,324 B2 | 11/2002 | Garofalo | |
| 6,532,603 B1 * | 3/2003 | Lan ............ 2/428 |

* cited by examiner

*Primary Examiner*—John J. Calvert
*Assistant Examiner*—Alissa J. Tompkins
(74) *Attorney, Agent, or Firm*—Leonard Tachner

(57) ABSTRACT

A dive mask having a pair of replaceable lenses comprises a soft, flexible skirt for bearing against the diver's face, an inner lens frame having a pair of openings for receiving the lenses and a peripheral member integrally molded into the skirt for permanent retention therein and a removable outer lens frame having a pair of lens openings and a peripheral member shaped to bear against the lenses adjacent the skirt. A sealing gasket is preferable molded into the inner lens frame along the lens openings to prevent water leakage into the face side of the lenses.

16 Claims, 7 Drawing Sheets

DIVE MASK HAVING REPLACEABLE LENSES AND FRAME BONDED INTO A RUBBER SKIRT

BACKGROUND OF THE INVENTION

1. Field of the Inveniton

The present invention relates generally to dive masks having two distinct lenses. The invention relates more specifically to a two window dive mask having an inner frame bonded directly into a rubber skirt and an outer frame to retain the lenses in place.

2. Background Art

The current state-of-the-art in dive masks employs either one of two construction methods. In the first, a rubber skirt is bonded directly to a single viewing lens (called frameless design). This single lens is the only rigid structural support for the mask. Only a single lens that covers both eyes can be used in this design because if two lenses were used, there would be nothing to keep the lenses aligned in the same plane. If the lenses are not on the same plane, distortion would occur when used underwater. The frameless design has the advantage of fewer parts, more streamlined appearance, lower cost construction, and no potential leak paths. It does not however allow removing or replacing lenses as they are permanently bonded in place. Replacing lenses is desirable to accommodate corrective lenses for those with less than perfect vision.

In the second method, a rigid plastic frame is mechanically attached to the rubber skirt and the rigid frame accepts one or two lenses with a sealing gasket and mechanical retainer to keep them in place (framed design). The frames are typically attached to the skirt with snap-fit plastic pieces or mechanical fasteners (screws). There exist two possible leak paths between the lenses and frame and between the frame and skirt. Framed masks typically provide poorer vision because of the bulk of the frame impinging upon the lens area.

An example of prior art dive masks designed to receive two corrective lenses which can be replaced to accommodate changes in correction, is disclosed in U.S. Pat. No. 6,484,324 to Garofolo. This patent teaches the use of a rubber skirt or face and two distinct frames referred to as a stiff body having a grooved relief extending beyond a pair of lenses and a frame which keeps the lenses in place. Having two distinct visible frames tends to result in a heavy and cumbersome-looking mask which is not hydrodynamic in appearance.

SUMMARY OF THE INVENTION

In the present invention, an internal plastic frame is bonded directly to the rubber skirt during the rubber molding process. The internal frame provides a receiver for the lenses and the structural member to keep them in the same plane. An outer frame is used to retain the lens or lenses in place.

The present invention provides a mask design which is simpler and has an easier assembly than the frame design.

The appearance can be made more streamlined and hydrodynamic like the frameless design because the inner frame is buried into the rubber skirt and does not project above the rubber surface. The inner frame can be smaller and lower profile than the type in a framed mask because it does not have to mechanically fit to or seat to the skirt.

Unlike other frameless masks, the internal frame allows a mechanism to interchange corrective lenses.

The leakage path between the frame and the skirt is eliminated.

An internal gasket can be molded into the inner frame during molding of the skirt. This eliminates a separate gasket.

Unlike the Garofalo patent mask referred to above, the present invention uses one visible exterior or outer frame to secure the lenses in place. A second interior or inner frame is invisible because it is essentially enclosed by the soft flexible skirt in which it is molded. Nevertheless, the interior frame provides a seating and structural support to hold two replaceable lenses in their proper orientation.

BRIEF DESCRIPTION OF THE DRAWINGS

The aforementioned objects and advantages of the present invention, as well as additional objects and advantages thereof, will be more fully understood herein after as a result of a detailed description of a preferred embodiment when taken in conjunction with the following drawings in which.

DETAILED DESCRIPTION OF A PREFERRED EMBODIMENT

Figure 1:
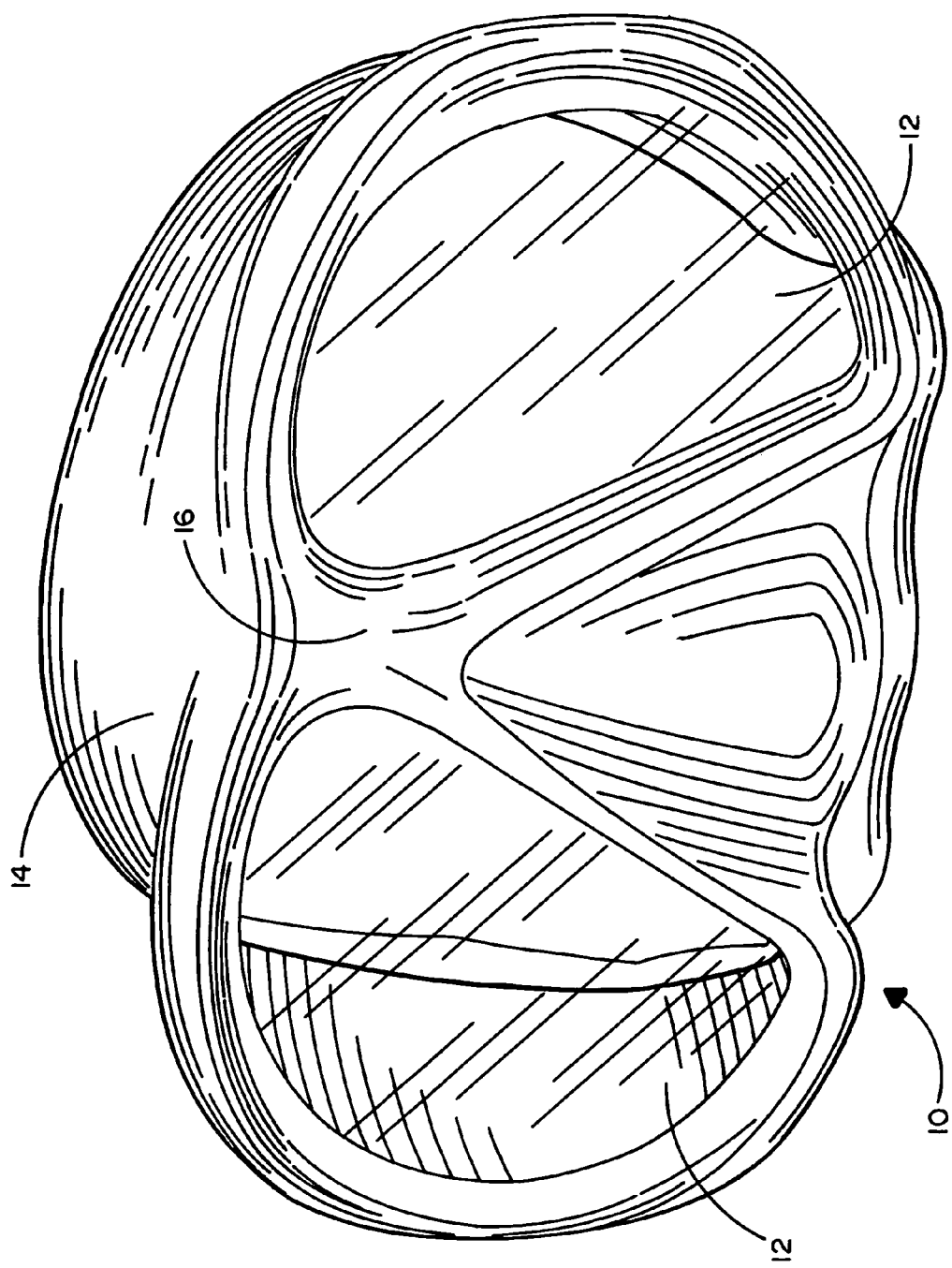
FIG. 1 is a three-dimensional front view of a preferred embodiment of the invention.

Referring to the accompanying figures and FIGS. 1–4 in particular, it will be seen that a dive mask 10 in accordance with a preferred embodiment of the invention is shown therein. As seen in FIGS. 1–4, mask 10 comprises a pair of lenses 12, a rubber-like soft flexible skirt 14, an outer frame 16, an inner frame 18 and a lens seal 20.

Figure 2:
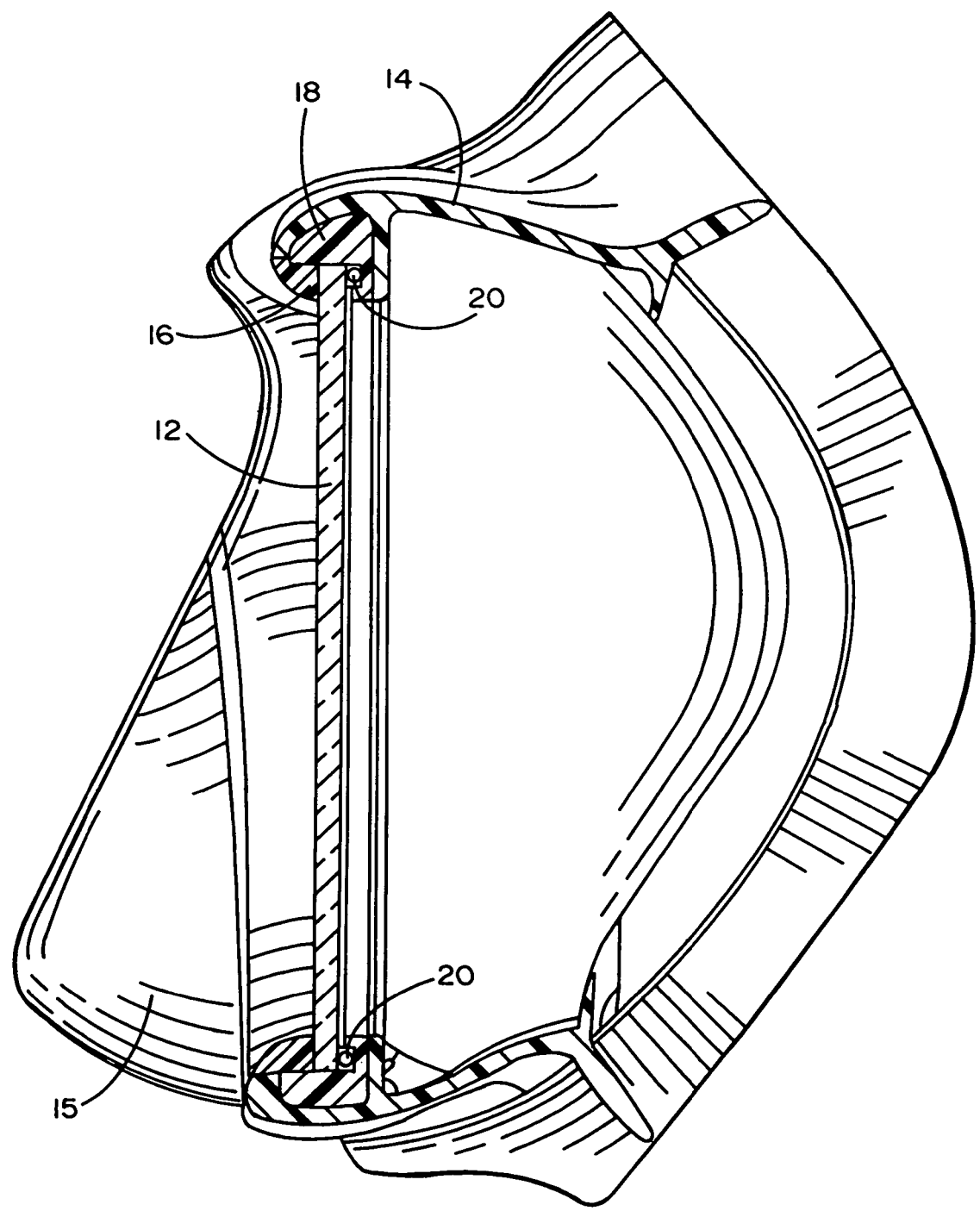
FIG. 2 is a side cross-sectional view thereof.
Figure 3:
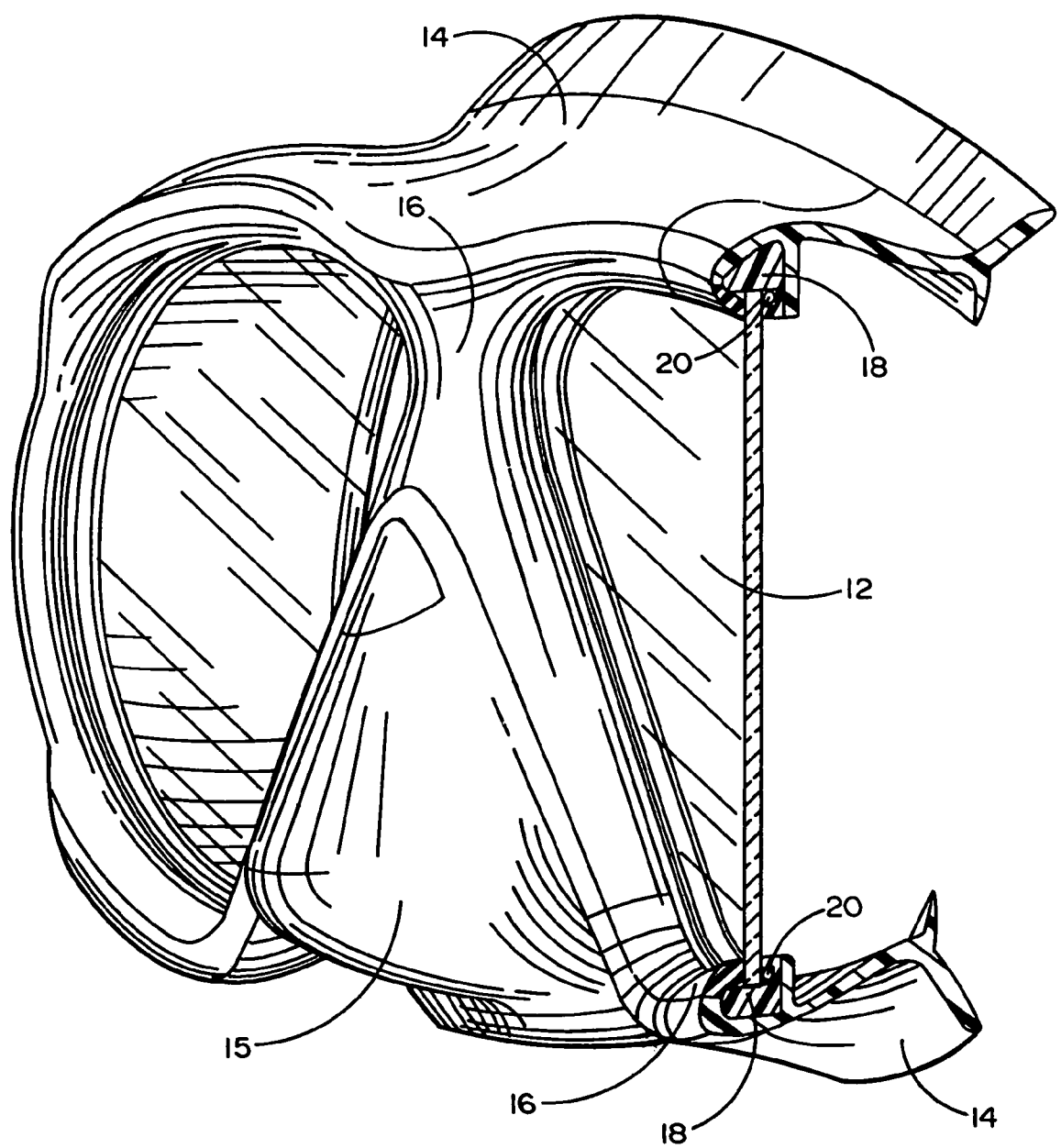
FIG. 3 is a three-dimensional cross-sectional view thereof.
Figure 4:
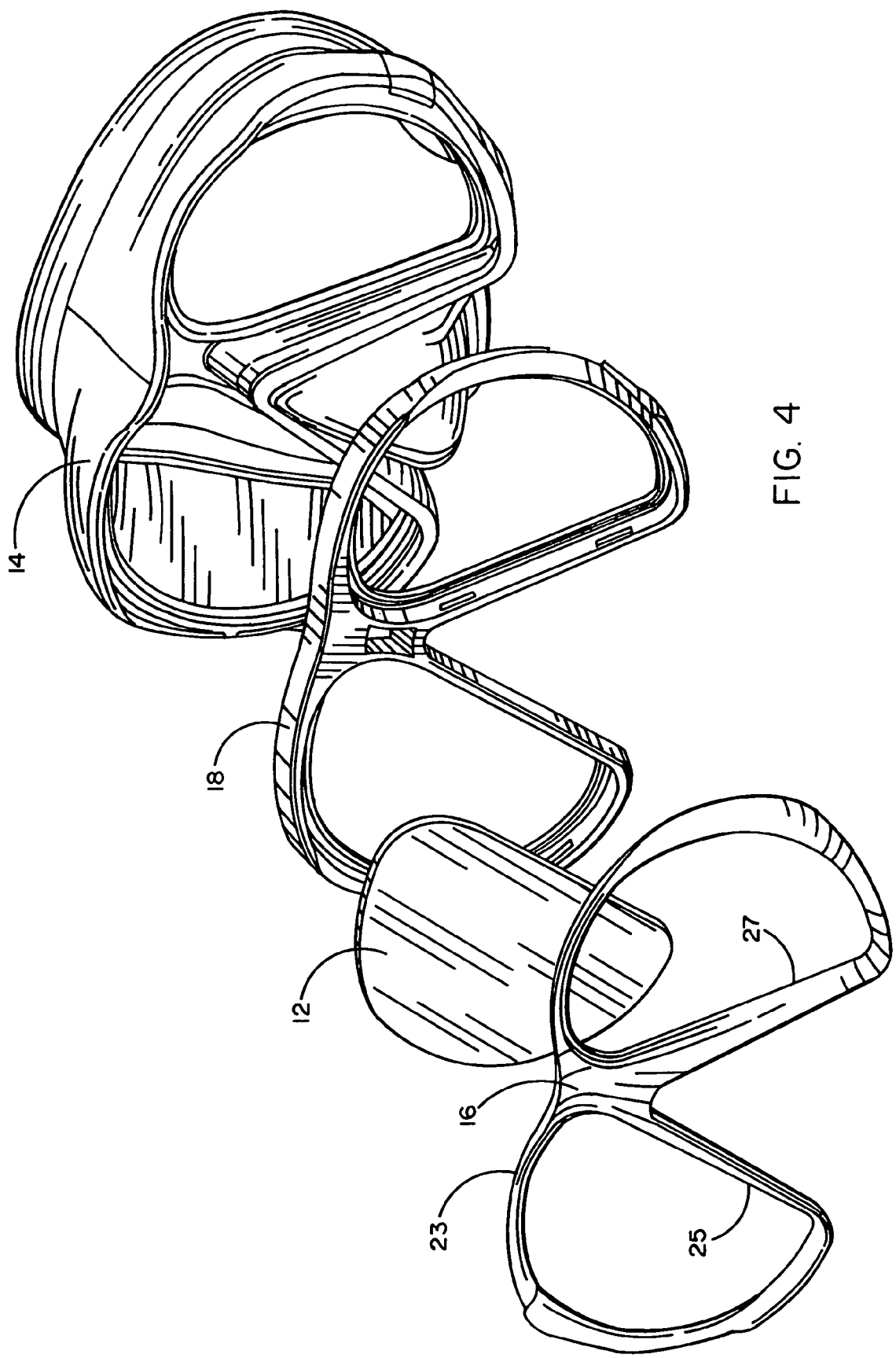
FIG. 4 is an exploded view thereof.

As seen best in FIGS. 2 and 3, inner frame 18 is actually bonded directly into rubber-like skirt 14 during the skirt molding process so that inner frame 18 is essentially surrounded by the skirt 14. Only the inner-facing and front-facing edges of the inner frame 18 are exposed. The inner-facing edges receive an internal gasket or lens seal 20. Gasket 20 is preferably molded onto inner frame 18 during the molding of the skirt thereby eliminating the need for a separate lens seal.

The inner frame 18 provides stiff receiving structure to hold the lenses 12 and prevent them from deviating from a common plane which could otherwise cause visual distortion. A peripheral member 21 is molded into the skirt 14.

The outer-facing edge of inner frame 18 receives an outer frame 16 which may be press fit against the outer periphery of the lenses 12 and over a nose piece 15 which forms part of the skirt 14. The outer frame 16 retains the lenses 12 in place and forces them against the sealing gasket 20, thereby forming a water-tight seal which prevents leakage into the region between the lenses and a diver's face. Outer frame 16 comprises a peripheral member 23 forming openings 25 and 27.

Figure 5:
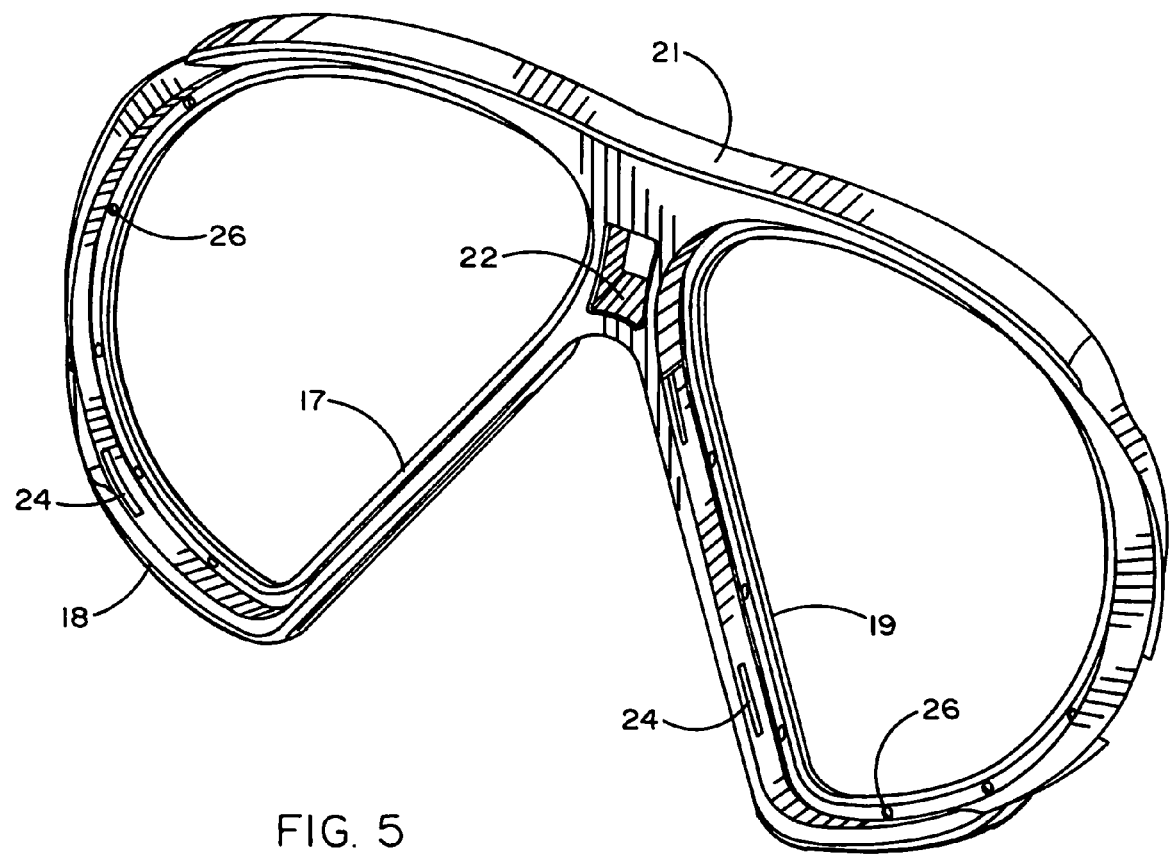
FIG. 5 is a front three-dimensional view of the inner frame of the preferred embodiment.
Figure 6:
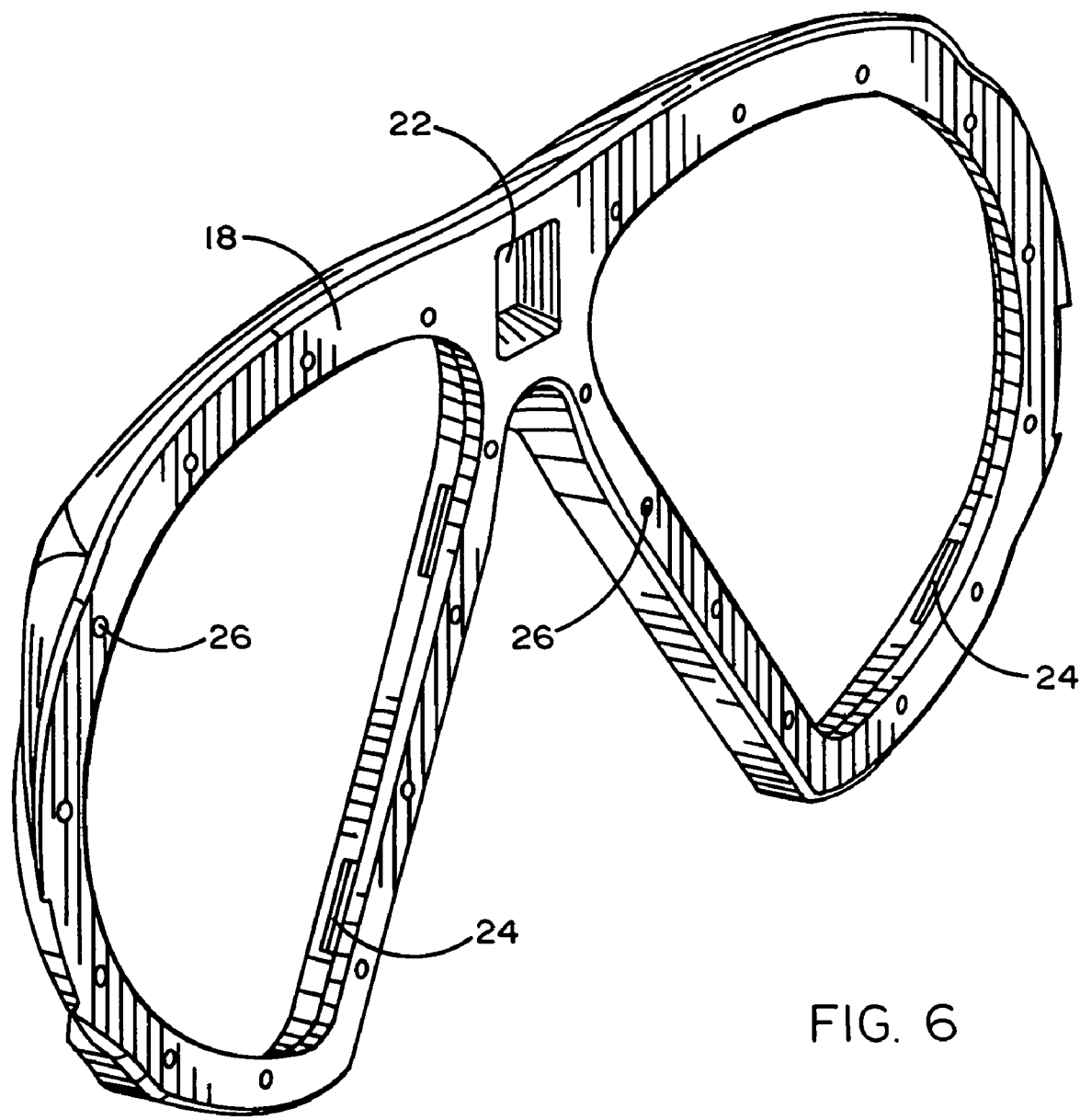
FIG. 6 is a rear three-dimensional view of the inner frame.

As seen best in FIGS. 5 and 6, inner frame 18 is preferably provided with a pair of lens receiving openings 17 and 19 that are generally shaped to be congruent with the lenses 12.

Frame 18 also has a main bonding aperture 22 and series of bonding recesses or grooves 24 and bonding through-holes 26. Aperture 22 as well as elongated recesses or grooves 24 and through-holes 26, assure flow-through bonding of the skirt and the frame 18 during the molding process to assure a permanent and durable bonding relationship between the frame and the skirt. It will be understood that once the inner frame 18 is molded into skirt 14, the inner frame is essentially entirely hidden from view thereby giving mask 10 the appearance of a frameless mask, but yet permitting the use of two separate lenses 12. Moreover, it will be apparent that by simply removing the outer frame 16, one may gain complete access to lenses 12 thereby permitting replacement of the lenses with lenses having corrective shapes or with lenses having different degrees of corrective characteristics to accommodate changes in optometric lens parameters.

Figure 7:
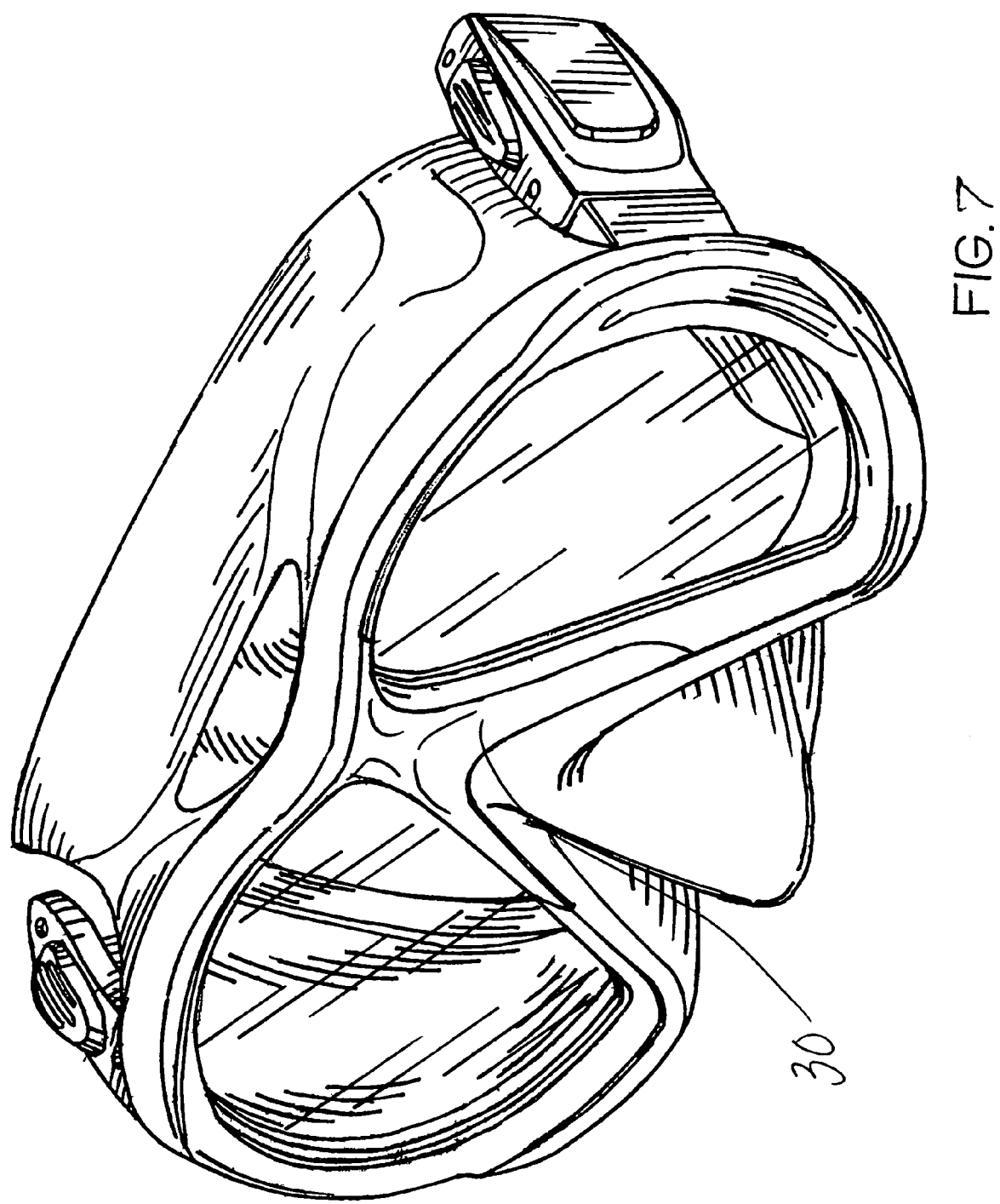
FIG. 7 is a front three-dimensional view showing the addition of a metal nose area support member.

The structure of the preferred embodiment may be further strengthened by employing rigidizing materials. For example, at least one of the frames may be molded of especially strong plastic material called "Grivory". A metal nose area support member may be affixed to at least one of the lens frames to further support the structure at its weakest point as shown in FIG. 7. It should also be noted that in practice it has been found useful to employ a second bridge mold of silicone that is layered between the inner lens frame and an outer bonded silicone skirt to promote a bonding link between materials that normally have difficulty in linking chemically.

Having thus disclosed a preferred embodiment to illustrate the inventive features of the present invention, it will now be apparent that various modifications and additions may be made. By way of example, while the disclosed embodiment has two separate lenses, it will be evident that the novel structure of the invention may be readily modified to accommodate one large lens covering both eyes. Accordingly, the scope hereof is to be limited only by the claims appended hereto and their equivalents.

What is claimed is:

1. A dive mask having at least one replaceable lens; the mask comprising:
   a soft flexible skirt for bearing against a diver's face;
   an inner lens frame defining a stiff receiving structure within said skirt to be obscured from a field of view having at least one first opening for receiving said at least one lens and a first peripheral member integrally molded into said skirt for permanent retention therein;
   a removable outer lens frame having at least one second opening allowing light to pass through to said at least one lens and a second peripheral member, said second peripheral member being shaped to bear against said lens adjacent said skirt with said at least one first opening and said at least one second opening being substantially aligned.

2. The dive mask recited in claim 1 further comprising a lens sealing gasket located between said inner lens frame adjacent said at least one first opening and said at least one lens.

3. The dive mask recited in claim 2 wherein said lens sealing gasket is permanently affixed to said inner lens frame along said at least one first opening.

4. The dive mask recited in claim 2 wherein said lens sealing gasket is molded into said inner lens frame along said at least one first opening.

5. A dive mask having a pair of replaceable lenses; the mask comprising:
   a soft flexible skirt for bearing against a diver's face;
   an inner lens frame defining a stiff receiving structure within said skirt to be obscured from a field of view having a pair of first openings for receiving said pair of lenses and a first peripheral member integrally molded into said skirt for permanent retention therein; and
   a removable outer lens frame having a pair of second openings allowing light to pass through to said pair of lenses and a second peripheral member being shaped to bear against said lenses adjacent said skirt with said first and second openings being substantially aligned.

6. The dive mask recited in claim 5 further comprising a lens sealing gasket located between said inner lens frame adjacent said first openings and said lenses.

7. The dive mask recited in claim 6 wherein said lens sealing gasket is permanently affixed to said inner lens frame along said first openings.

8. The dive mask recited in claim 6 wherein said lens sealing gasket is molded into said inner lens frame along said first openings.

9. The dive mask recited in claim 5 further comprising a metal nose area support member mechanically affixed to at least one of said outer and inner lens frames.

10. A dive mask having at least one replaceable lens; the mask comprising:
    a soft flexible skirt for bearing against a diver's face;
    an inner lens frame having at least one first opening for receiving said at least one lens and a first peripheral member integrally molded into said skirt for permanent retention therein;
    a removable outer lens frame having at least one second opening allowing light to pass through to said at least one lens and a second peripheral member, said second peripheral member being shaped to bear at least partially against each of said lens, skirt, and inner lens frame, with said at least one first opening and said at least one second opening being substantially aligned.

11. The dive mask recited in claim 10 further comprising a lens sealing gasket located between said inner lens frame adjacent said at least one first opening and said at least one lens.

12. The dive mask recited in claim 11 wherein said lens sealing gasket is permanently affixed to said inner lens frame along said at least one first opening.

13. The dive mask recited in claim 12 wherein said lens sealing gasket is molded into said inner lens frame along said at least one first opening.

14. The dive mask recited in claim 13 further comprising a metal nose area support member mechanically affixed to at least one of said outer and inner lens frames.

15. The dive mask recited in claim 10 wherein said second peripheral member includes a pair of bearing surfaces extending transversely from a common edge for conformingly engaging respective portions of said lens and inner lens frame.

16. The dive mask recited in claim 15 wherein one of said bearing surfaces extends beyond said inner lens frame to conformingly engage a portion of said skirt disposed adjacent thereto.

* * * * *